(12) United States Patent
Kamen et al.

(10) Patent No.: US 6,234,997 B1
(45) Date of Patent: May 22, 2001

(54) SYSTEM AND METHOD FOR MIXING AND DELIVERING INTRAVENOUS DRUGS

(75) Inventors: Dean L. Kamen, Bedford, NH (US); Charles M. Grinnell, Groton, MA (US); Marc A. Mandro, Bow, NH (US); Dennis Gilbreath, Concord, NH (US); Kevin Grant, Manchester, NH (US); Jason A. Demers, Manchester, NH (US); William T. Larkins, Manchester, NH (US); Robert Manning, Pembroke, NH (US); Richard Lanigan, Concord, NH (US)

(73) Assignee: Deka Products Limited Partnership, Manchester, NH (US)

( * ) Notice: Subject to any disclaimer, the term of this patent is extended or adjusted under 35 U.S.C. 154(b) by 0 days.

(21) Appl. No.: 09/359,237

(22) Filed: Jul. 22, 1999

Related U.S. Application Data

(60) Division of application No. 09/137,025, filed on Aug. 20, 1998, which is a continuation-in-part of application No. 08/916,890, filed on Aug. 22, 1997, now abandoned, which is a continuation-in-part of application No. 08/917,537, filed on Aug. 22, 1997, now Pat. No. 6,165,154, which is a continuation-in-part of application No. 08/478,065, filed on Jun. 7, 1995, now Pat. No. 5,755,683.

(51) Int. Cl.$^7$ .................................................. A61M 37/00

(52) U.S. Cl. ............................................. 604/131; 604/82

(58) Field of Search ........................ 604/131, 82, 87–92, 604/80, 81, 416

(56) References Cited

U.S. PATENT DOCUMENTS 3,570,486 * 3/1971 Engelsher ............................ 128/215

(List continued on next page.)

FOREIGN PATENT DOCUMENTS

| 36 05 640 | 8/1987 | (DE) | ................................ B67C/1/06 |
| 0 154 191 | 9/1985 | (EP) | ................................ A61M/5/14 |

(List continued on next page.)

OTHER PUBLICATIONS

Edmond, et al., "Prevention of Mis–Prescribing in the Elderly: A Potential Use for Micro–Computers", Proceedings of the 8$^{th}$ Annual Sumposium on Computer Applications in Medical Care, Washington, DC, USA, Nov. 4–7, 1984, 357–360.

(List continued on next page.)

*Primary Examiner*—Sharon Kennedy
(74) *Attorney, Agent, or Firm*—Bromberg & Sunstein LLP

(57) ABSTRACT

A bedside-pharmacy system for the preparation and delivery of intravenous drugs. The system includes a liquid inlet for connection to a liquid supply, vial receptacles, and a liquid outlet for providing the intravenous drug in mixed, liquid form to the patient. The system may include a chamber having a variable volume, and a valve mechanism, which may be actuated to control flow between the liquid outlet, the variable-volume chamber, the vial receptacles and the liquid inlet. The system induces change in the volume of the variable-volume chamber and actuates the valve mechanism, so as to introduce liquid from the liquid inlet into the vials and reconstitute or dilute the drugs and so as to deliver the drugs to the patient. In a preferred embodiment, the liquid inlet, the vial receptacles, the variable-volume chamber, the liquid outlet and the valve mechanism (in other words, all components that come into contact with the liquid) are located in a disposable cassette, which may be received in a control unit. The system may include means for changing the chamber volume and actuating the valves so as to move the liquid repeatedly between a vial and the chamber. After the drug has been reconstituted, the system may cause the drug to be further diluted by providing an additional volume of liquid to be mixed with the drug. The system may further include a second chamber for delivery of the drug to the patient in precise quantities.

4 Claims, 7 Drawing Sheets

U.S. PATENT DOCUMENTS

| | | | | |
|---|---|---|---|---|
| 4,534,764 | * | 8/1985 | Mittleman et al. | 604/81 |
| 4,573,994 | | 3/1986 | Fischell et al. | 604/891 |
| 4,576,211 | | 3/1986 | Valentini et al. | 141/329 |
| 4,721,138 | | 1/1988 | Simonazzi | 141/150 |
| 4,804,366 | | 2/1989 | Zdeb et al. | 604/85 |
| 4,850,978 | | 7/1989 | Dudar et al. | 604/201 |
| 4,925,444 | | 5/1990 | Orkin et al. | 604/250 |
| 5,006,050 | | 4/1991 | Cooke et al. | 417/478 |
| 5,062,774 | | 11/1991 | Kramer et al. | 417/413 |
| 5,088,515 | | 2/1992 | Kamen | 137/15 |
| 5,116,316 | | 5/1992 | Sertic et al. | 604/83 |
| 5,122,116 | * | 6/1992 | Kriesel et al. | 604/89 |
| 5,330,426 | * | 7/1994 | Kriesel et al. | 604/89 |
| 5,385,540 | | 1/1995 | Abbot et al. | 604/4 |
| 5,401,059 | | 3/1995 | Ferrario | 283/67 |
| 5,478,337 | * | 12/1995 | Okamoto et al. | 604/413 |
| 5,651,775 | | 7/1997 | Walker et al. | 604/207 |
| 5,681,285 | | 10/1997 | Ford et al. | 604/151 |
| 5,713,865 | | 2/1998 | Manning et al. | 604/122 |
| 5,755,683 | | 5/1998 | Houle et al. | 604/30 |
| 5,758,095 | | 5/1998 | Albaum et al. | 395/202 |
| 5,776,103 | * | 7/1998 | Kriesel et al. | 604/132 |
| 5,879,328 | * | 3/1999 | Holmberg et al. | 604/82 |

FOREIGN PATENT DOCUMENTS

| | | | |
|---|---|---|---|
| 0 335 378 | 10/1989 | (EP) | A61J/1/00 |
| 2 717 919 | 9/1995 | (FR) | G06F/7/60 |
| WO93/12825 | 7/1993 | (WO) | A61M/1/00 |
| WO94/08549 | 4/1994 | (WO) | A61J/1/00 |
| WO94/12235 | 6/1994 | (WO) | A61M/31/00 |
| WO95/29455 | 11/1995 | (WO) | G06F/159/00 |
| WO96/13790 | 5/1996 | (WO) | G06F/159/00 |
| WO96/40328 | 12/1996 | (WO) | A61M/5/168 |
| WO97/04712 | 2/1997 | (WO) | A61B/19/00 |

OTHER PUBLICATIONS

Ogura, et al., "One–line Prescription Order and Prescription Support in an Integrated Hospital Information System", Med. Inform. (1985) vol. 10, No. 4, 287–299.

Moliver, et al., "Decision Support for Medical Treatment: A TPN Prescription System on a Central Hospital Computer", Proceedings of the 11$^{th}$ Annual Symposium on Computer Applications in Medical Care, Washington, DC, USA, Nov. 1–4, 1987, 246–254.

Ogura, et al., "Online Support Functions of Prescription Order System and Prescription Audit in an Integrated Hospital Information System", Med. Inform. (1988), vol. 13, No. 3, 161–169.

* cited by examiner

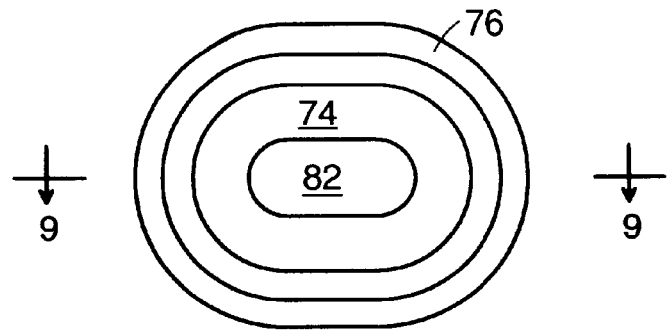
FIG. 8
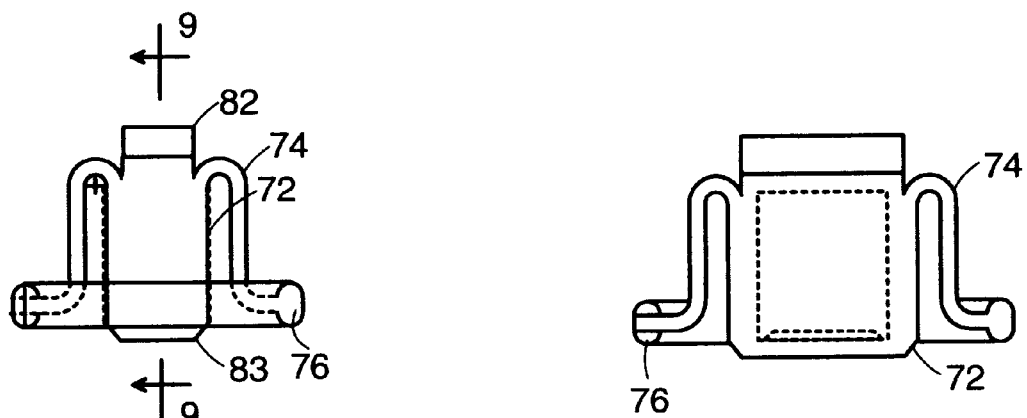
FIG. 7
FIG. 9
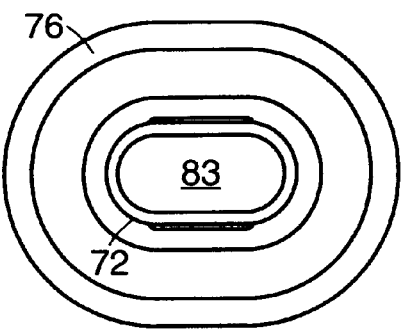
FIG. 10

SYSTEM AND METHOD FOR MIXING AND DELIVERING INTRAVENOUS DRUGS

RELATED APPLICATIONS

The present application is a divisional of application Ser. No. 09/137,025, filed Aug. 20, 1998, which is a continuation-in-part of U.S. patent application Ser. Nos. 08/916,890 abandoned and 08/917,537 now U.S. Pat. No. 6,165,154, both of which were filed Aug. 22, 1997, which is a C-I-P of Ser. No. 08/478,065 filed Jun. 7, 1995 U.S. Pat. No. 5,755,683. These applications are incorporated herein by reference.

TECHNICAL FIELD

The present invention relates to devices and methods for the preparation and delivery of intravenous drugs.

SUMMARY OF THE INVENTION

The invention is directed to a system, which may be located adjacent a patient's bed (or chair), for preparing and delivering an intravenous drug from a vial to the patient. The system includes a liquid inlet for connection to a liquid supply, at least (and preferably more than) one vial receptacle, and a liquid outlet for providing the intravenous drug in mixed, liquid form to the patient. Preferably, the system includes a chamber having a variable volume, and a valve mechanism, which may be actuated to control flow between the liquid outlet, the variable-volume chamber, the vial receptacle and the liquid inlet. The system induces change in the volume of the variable-volume chamber and actuates the valve mechanism, so as to introduce liquid from the liquid inlet into the vial and reconstitute or dilute the drug and so as to deliver the drug to the patient. In a preferred embodiment, the liquid inlet, the vial receptacle, the variable-volume chamber, the liquid outlet and the valve mechanism (in other words, all components that come into contact with the liquid) are located in a disposable cassette, which may be received in a control unit.

In order to ensure that a powdered drug is completely reconstituted, the system preferably includes means for changing the chamber volume and actuating the valves so as to move the liquid repeatedly between the vial and the chamber. After the drug has been reconstituted, the system may cause the drug to be further diluted by providing an additional volume of liquid to be mixed with the drug. In a preferred embodiment, the system further includes a second chamber, and the additional volume of liquid is mixed with the drug in the second chamber. This second chamber preferably has a variable-volume as well. A primary purpose of such a second chamber (the delivery chamber) is to deliver the drug to the patient in precise quantities. The primary purpose of the first chamber (the mixing chamber) is to mix and reconstitute the drugs. To accomplish these purposes, the mixing chamber preferably has a larger volume than the delivery chamber.

Both variable-volume chambers are preferably defined by a rigid wall and a flexible membrane. Preferably, a groove is defined in the rigid wall between the conduits leading into and out of the variable-volume chambers. In the mixing chamber, the groove may be made shallow adjacent the upper conduit and wide adjacent the lower conduit, in order to promote the flow of air and liquid from the top and bottom of the mixing chamber respectively.

The disposable cassette preferably has a first valve chamber defined by a first rigid wall and a first flexible membrane, and a second valve chamber defined by a second rigid wall and a second flexible membrane; and the control unit preferably has a cam, a first actuator disposed adjacent the first flexible membrane so that movement of the first actuator causes a change in pressure on the first flexible membrane, and a second actuator disposed adjacent the second flexible membrane so that movement of the second actuator causes a change in pressure on the second flexible membrane, wherein the cam and actuators are disposed with respect to each other such that, as the cam is rotated, the actuators are moved. The cam is preferably shaped so that at any time at least one actuator is urging the corresponding flexible membrane into a closed position. The valves may be located at the inlet and outlet ends of the variable-volume chamber where the flow-rate of liquid to the patient is measured, so that liquid cannot flow through the system without being measured.

The cassette also includes, in a preferred embodiment, an outlet free-flow-prevention valve which is permanently closed to prevent flow through the outlet when the cassette is removed from a control unit which actuates the valve. Preferably, the outlet free-flow-prevention valve includes a valve chamber defined by a rigid portion of the cassette and a membrane, wherein the membrane includes a folded portion that extends towards the outside of the cassette, so that when an actuator from the control unit pushes the folded portion the membrane collapses into the valve chamber so as to restrict flow therethrough. In a further preferred embodiment, the cassette includes an inlet free-flow-prevention valve which is permanently closed to prevent flow through the liquid inlet when the cassette is removed from the control unit.

In order to ensure that all of a drug is delivered to a patient, it is important that all of the drug be purged from a manifold portion of the passageways in the cassette. A preferred method of accomplishing this purging is to further provide the cassette with an air vent in fluid communication with the manifold, an inlet valve controlling flow between the mixing chamber and the manifold, and an air valve controlling flow between the air vent and the manifold. After several volumes of medication are moved from a vial through the manifold to the mixing chamber, air is urged from the vent through the manifold to force substantially all the medication from the manifold into the mixing chamber.

Although the reconstituted drug may be delivered from the vial to the patient, preferably fluid is drawn from the vial to the mixing chamber for dilution to the proper concentration. Preferably, the diluted drug is then delivered from the mixing chamber to the delivery chamber, from which the final dose of medication may be delivered to the patient. As noted above, in alternative embodiments, a separate delivery chamber is not necessary, and the mixing chamber may deliver the diluted drug directly to the patient.

BRIEF DESCRIPTION OF THE DRAWINGS

FIG. 7 is a left side view of a membrane used in the free-flow-prevention valve of the cassette of FIG. 2.

FIG. 8 is a rear view of the membrane of FIG. 7.

FIG. 9 is a cross-sectional view of the membrane shown in FIGS. 7 and 8 across lines 9—9.

FIG. 10 is a front view of the membrane of FIG. 7.

DETAILED DESCRIPTION OF SPECIFIC EMBODIMENT

Figure 1:
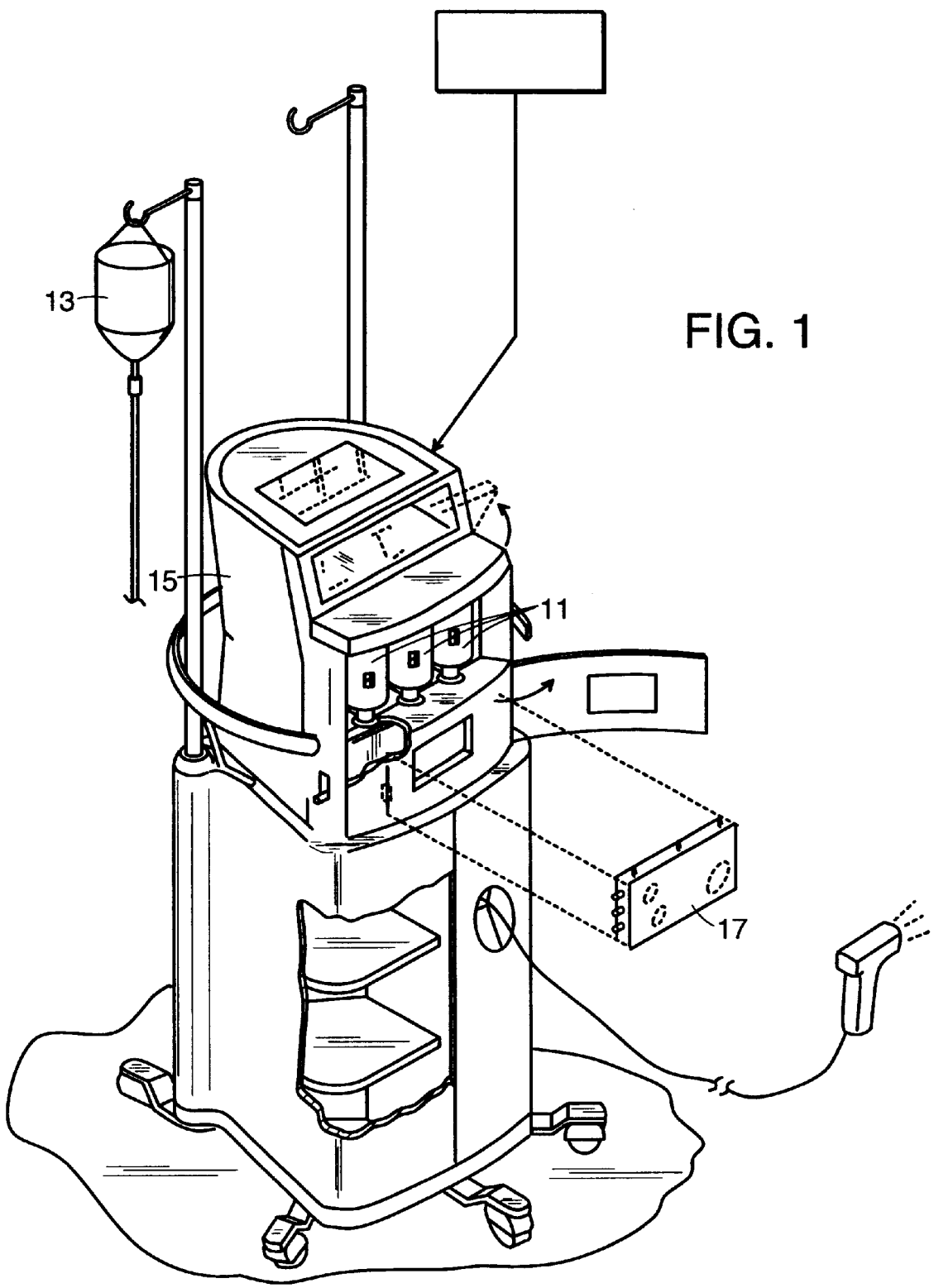
FIG. 1 is a perspective view of a system according to a preferred embodiment of the present invention.

FIG. 1 shows a system for the preparation and delivery of drugs according to a preferred embodiment of the invention. Powdered drugs are provided in vials 11 and are mixed by the system with a liquid provided in container 13. The system includes a disposable cassette 17, which is disposed of between patients, and a control unit 15, which receives and controls the cassette, and which is used over and over. In general, liquid flows from container 13, is directed by the cassette 17 to a vial 11 so as to reconstitute the powdered drug or dilute a liquid drug to its proper concentration, and then is directed by the cassette to the patient. During periods of the drug-delivery cycle, liquid from container 13 may be directed by cassette 17 directly to the patient without being mixed with a drug. Premixed drugs may be delivered by the system from the vials to the patient and from a bag connected to a luer port (item 26 in FIGS. 2 and 3) on the cassette. The specific embodiment discussed herein uses separate mixing and delivery chambers. It will be appreciated by one of ordinary skill in the art, that a single variable-volume chamber may be used to accomplish both mixing and delivering.

Figure 2:
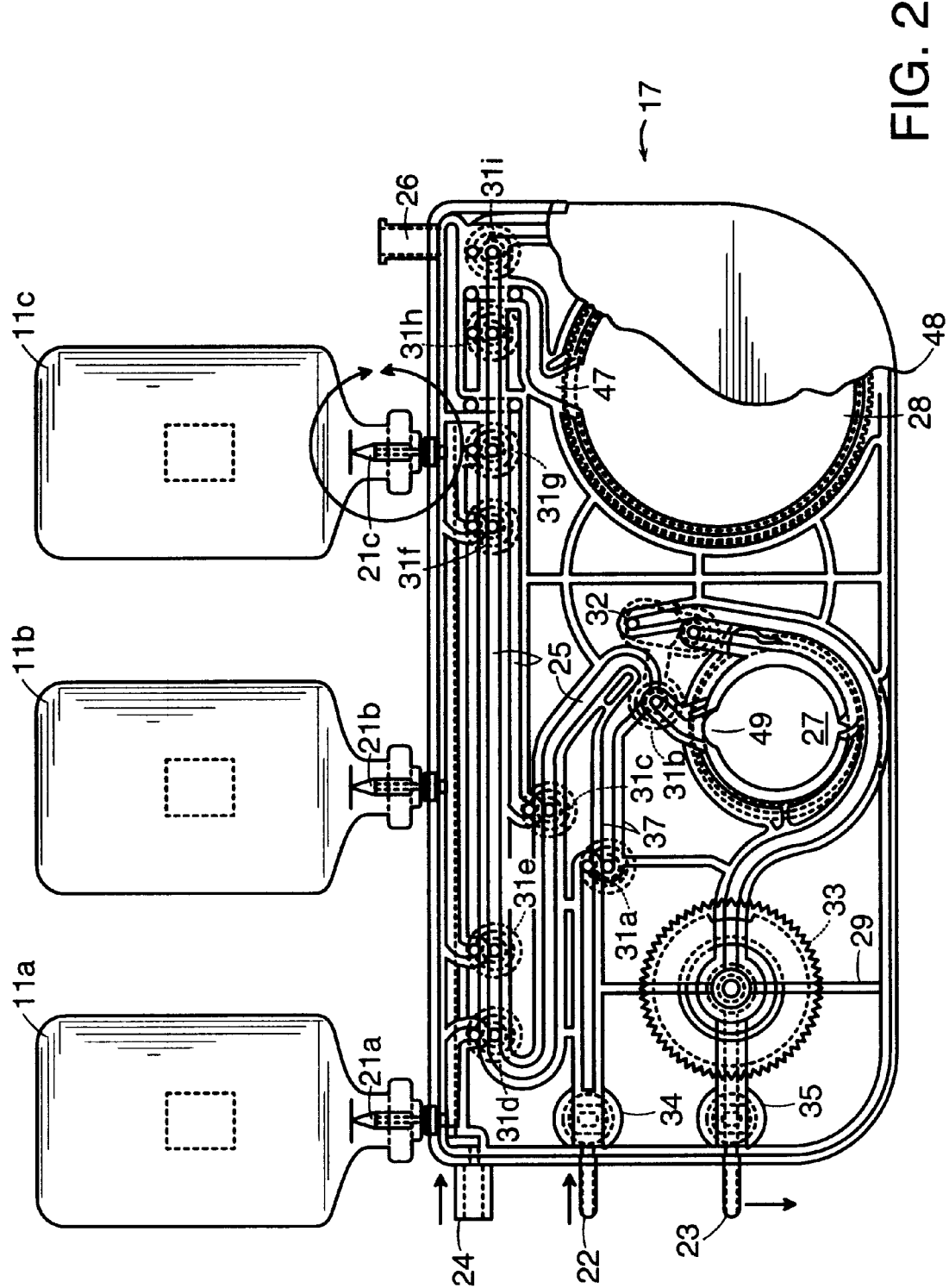
FIG. 2 is a rear view of the cassette that may be used in the system of FIG. 1, along with three vials attached to the cassette.
Figure 3:
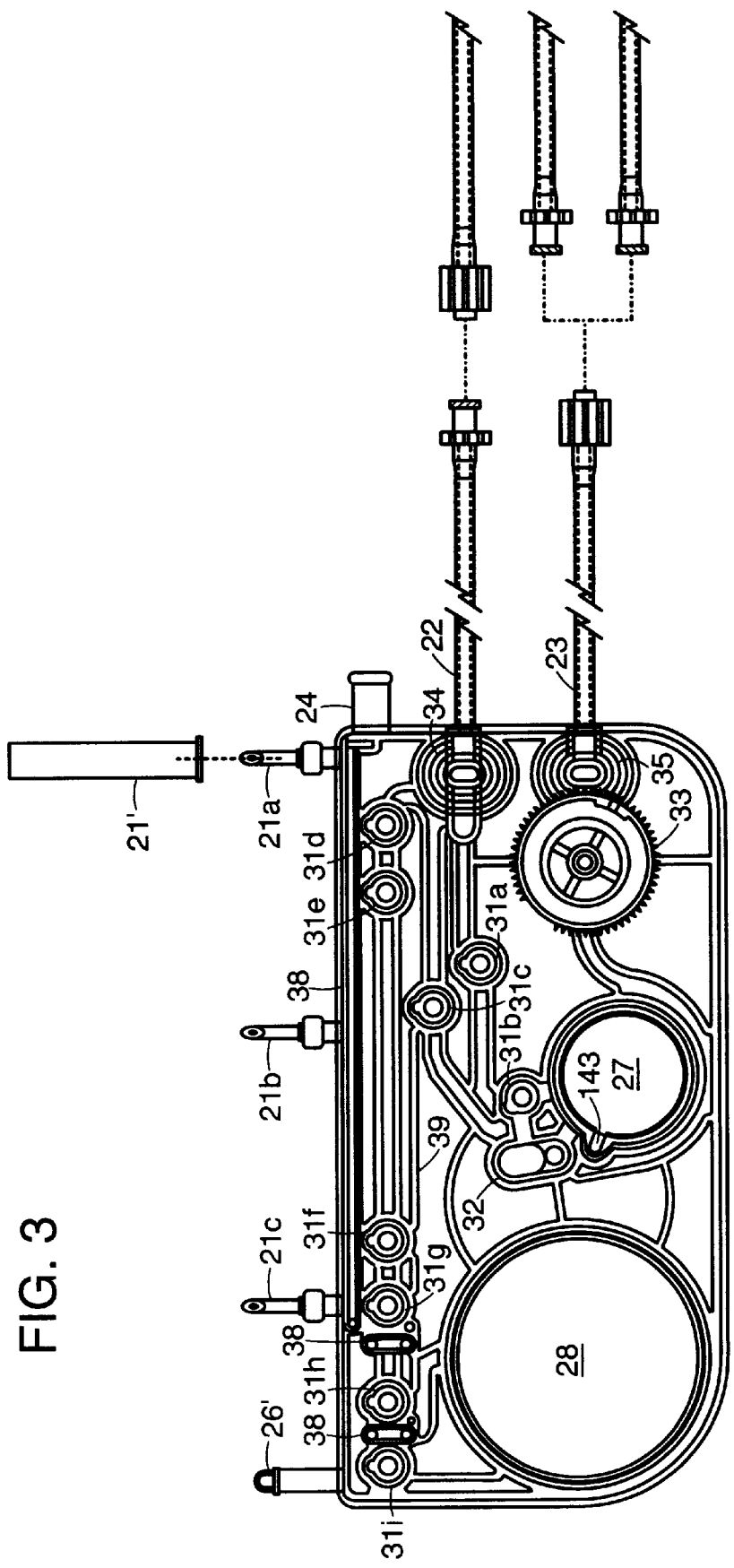
FIG. 3 is a front view of a cassette that may be used in the system of FIG. 1.
Figure 3A:
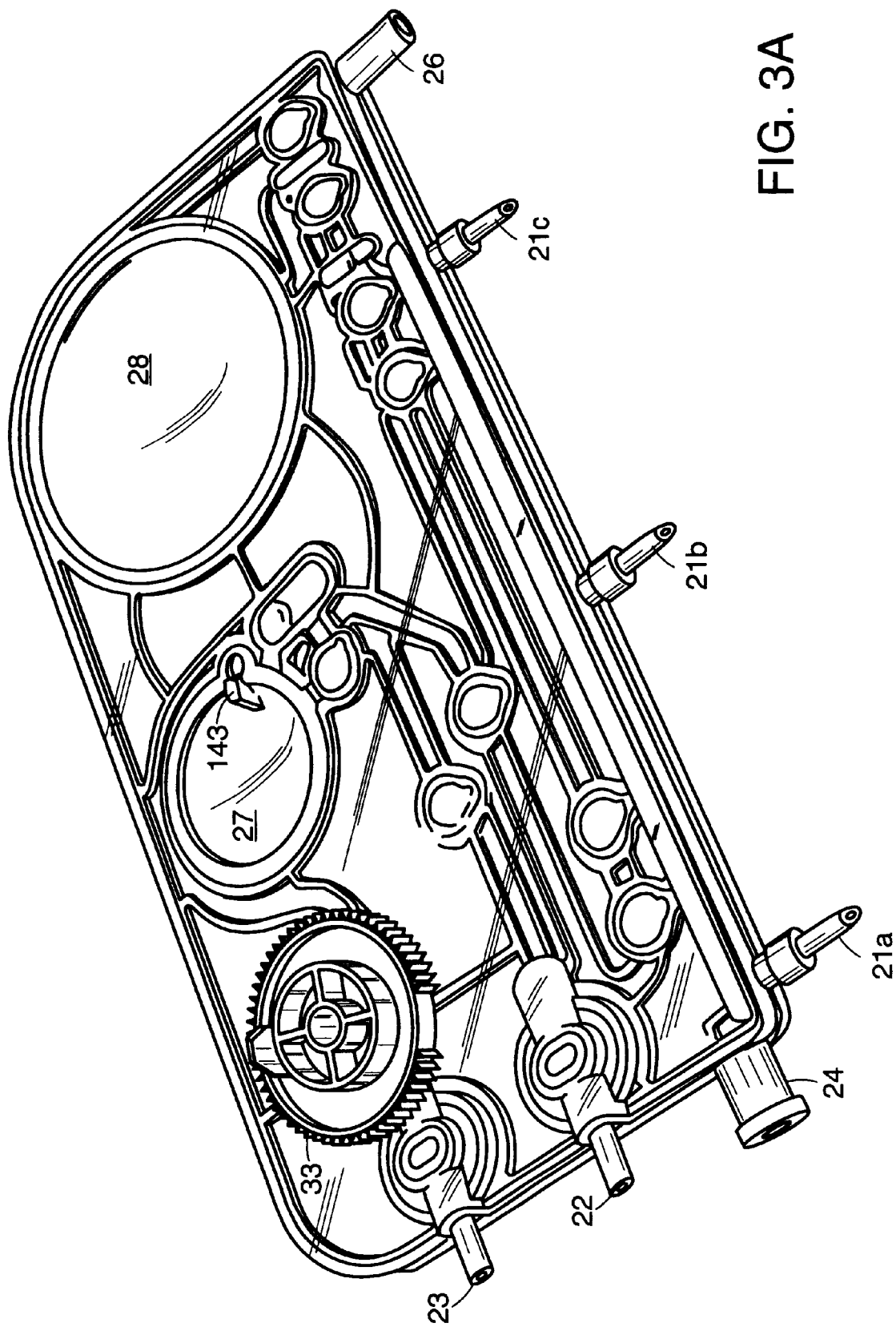
FIG. 3A is a perspective view of the cassette of FIG. 3.

FIG. 2 shows a rear view of a cassette 17 that may be used in the system of FIG. 1. (i.e., FIG. 2 shows the side of the cassette that faces away from the control unit 15.) FIG. 3 shows a front view (i.e., the control-unit side) of a cassette 17, and FIG. 3A shows a perspective view of the cassette. Some of the features used in this cassette 17 are also used in the cassette disclosed in above-referenced U.S. application Ser. No. 08/917,537 for "Cassette for Intravenous-Line Flow-Control System," and its parent, U.S. application Ser. No. 08/478,065 filed Jun. 7, 1995 now U.S. Pat. No. 5,755,683, issued May 26, 1998. FIG. 2 shows three vials 11a–11c attached respectively to spikes 21a–21c. Liquid entering the cassette 17 from container 13 (shown in FIG. 1) passes through port 22, and liquid going to the patient exits the cassette through port 23. An air vent 24 permits air to be drawn into the cassette to be directed into a vial to replace liquid leaving the vial or to be directed through the cassette's passageways 25 in order to remove any liquid in the passageways. A luer port 26 permits a premixed drug container or alternate diluent source to be attached to the cassette. The cassette has two pressure-conduction chambers: a delivery chamber 27 and a mixing chamber 28, both of which are covered by a flexible membrane.

Valves 31a–31i control flow through the passageways 25. These valves 31a–31i are preferably membrane-covered valves of the type shown in FIGS. 1 and 9 of U.S. Pat. No. 5,088,515. The membranes of these valves 31a–31i may be forced into a closed position by pressure exerted by the control unit. This pressure may be positive air pressure provided by the control unit, or in one preferred embodiment, the pressure may be exerted by a mechanical actuator mounted in the control unit.

Valves 31b and 32 control flow into and out of delivery chamber 27. In a preferred embodiment, these two valves 31b and 32 are each controlled by an actuator, and these two actuators are controlled by a single cam. The cam and the actuators are arranged so that, at all times, at least one of valves 31b and 32 is closed. In other words, sometimes both valves are closed, sometimes one valve is opened and the other is closed, but both valves are never opened at the same time. Such an arrangement assures that liquid does not free flow through the delivery chamber.

Valve 32 controls flow from the delivery chamber 27 to the patient. Valve 32 is preferably of the type shown in FIGS. 18 and 19 of U.S. Pat. No. 5,755,683. The membrane of valve 32 has a portion that, when actuated by the control unit, seals off the mouth located within the valving chamber (in the same manner as valves 31a–31i) and another portion that is more compliant. Valve 32 works in conjunction with the stopcock valve 33, so as to smooth out the delivery of fluid, in the manner described in U.S. Pat. No. 5,755,683. The control unit includes a wheel or other mechanism for receiving and rotating the cassette's stopcock valve 33.

Similar to the cassette described in U.S. Pat. No. 5,755,683, the body of the cassette 17 shown in FIGS. 2 and 3 is preferably made from three thermoplastic layers ultrasonically welded together. Most of the passageways 25 are formed between the back layer and the middle layer and are defined by the back and middle layers and channel walls 37. In a preferred embodiment, the channel walls 37 extend from the middle layer and are sealingly attached to the back layer by an ultrasonic weld. Some of the walls 29 between the back and middle layers do not define passageways but merely provide structural rigidity. The front and middle layers define several sections 38 of the fluid passageways, and the front and middle layers hold the membranes for the delivery chamber 27, the mixing chamber 28 and the valves 31a–31i, 32. Walls 39 are provided on the front side of the middle layer to permit easier ultrasonic welding of the channel walls between the back and middle layers.

Each of the vial spikes 21a–21c may be provided with a spike cap 21' to keep the cassette and spikes safe and sterile during storage and handling. Similarly, the luer port 26 may be provided with a cap 26' to keep the cassette sterile.

The inlet port 22 and the outlet port 23 are respectively provided with free-flow-prevention valves 34 and 35, which are automatically closed by the control unit when the door holding the cassette is opened. These free-flow-prevention valves are discussed in greater detail below in connection with FIGS. 7–10.

Figure 4:
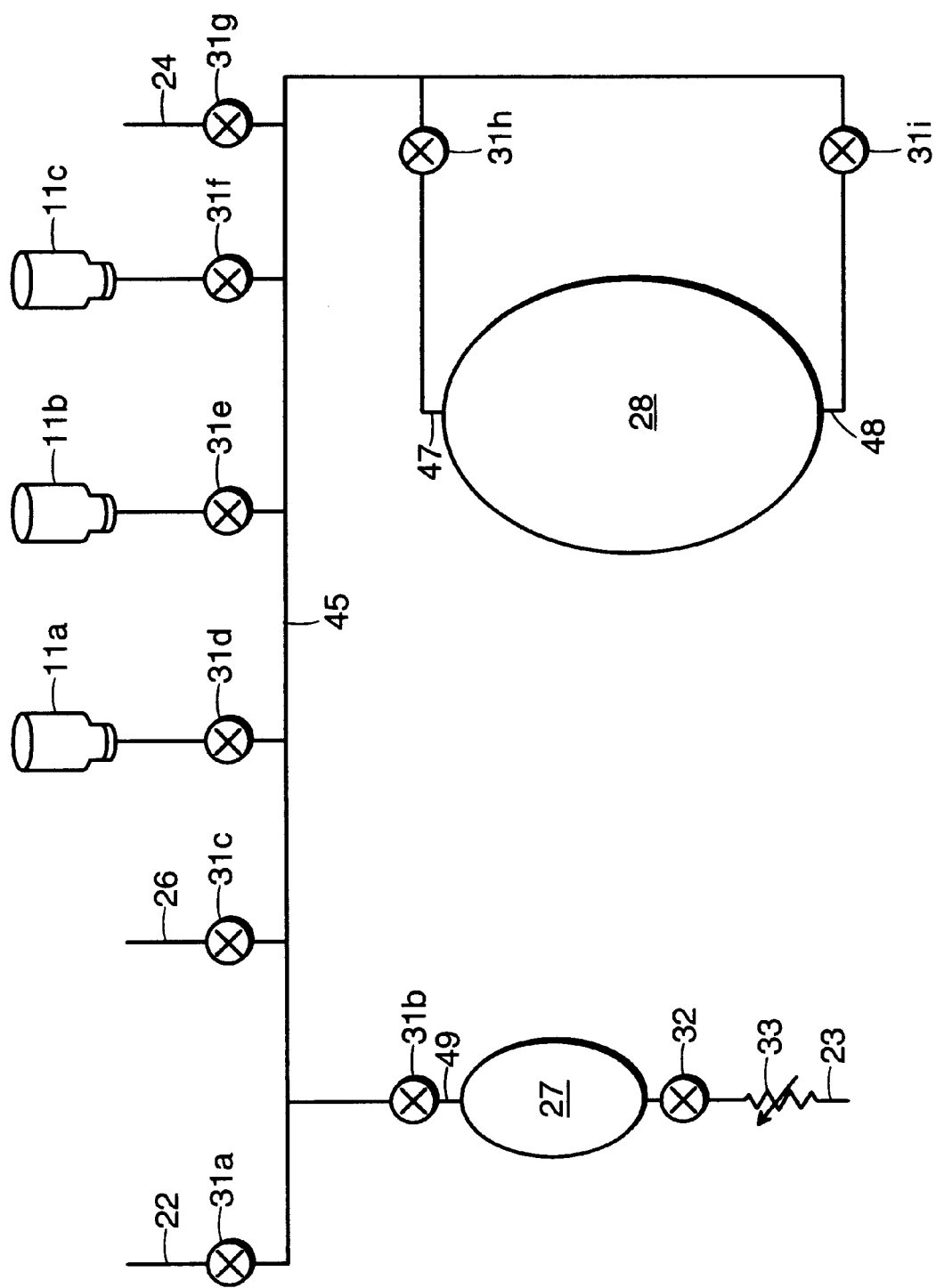
FIG. 4 is a schematic showing the fluid pathways through the cassette of FIG. 3.

FIG. 4 is a schematic showing how the valves control the flow of fluid through the cassette shown in FIGS. 2 and 3. In a typical application, the inlet 22 of the cassette is attached to an IV solution source (item 13 in FIG. 1), the luer port is connected to a liquid medicine supply, and each of the spikes (items 21a–21c in FIG. 3) may be attached to a vial 11a–11c containing a powdered drug that must be reconstituted by the IV solution source or containing a liquid drug that may or may not need to be diluted before being delivered to the patient.

Dilution is performed by pulling liquid from the solution source (item 13 in FIG. 1) and the vial to the mixing chamber in the appropriate proportions. Of course, it is important that the drugs be diluted the correct amount so as to avoid sending to the patient a drug solution that is too concentrated or too diluted. To ensure the correct amount of dilution, liquid from the IV solution source is measured in the delivery chamber 27 before being sent to the mixing chamber.

An example of a typical drug-delivery cycle first prepares the drug from vial 11a for delivery to the patient, then the drug from vial 11b, then the drug from vial 11c and then the liquid drug provided through the luer port 26. (Of course, variations of this drug-delivery cycle may be implemented.) To implement such a cycle, the control unit (item 15 of FIG. 1) actuates the membrane-based valves 31a–31i and 32, as well as the stopcock valve 33.

After the cassette has been primed, valves 31a and 31b are opened (with all the other membrane-based valves 31c–31i, 32 kept closed), and the control unit applies a negative pressure for a specified amount of time against the membrane of the delivery chamber 27, so as to draw liquid from the IV solution source into the delivery chamber. In a preferred embodiment, the rigid wall defining the variable-volume delivery chamber includes a bulge or other irregularity to make the membrane defining the delivery chamber less stable when the chamber is at its lowest volume; this instability makes it easier for the membrane to be pulled away from the rigid portion. Such a cassette may also use a membrane having a pressure-reduction tab 143, which creates some instability in the filled-chamber position and which may be actuated to create some instability in the empty-chamber position.

After a sufficient amount of liquid has been introduced into the delivery chamber 27, valve 31a is closed, and the control unit uses, for example, the bubble-detection method taught in U.S. patent application Ser. No. 08/477,380 filed Jun. 7, 1995 now U.S. Pat. No. 5,641,892, issued Jun. 24, 1997 (which is incorporated herein by reference) to determine whether there is any air in the delivery chamber 27. If there is any air bubble in the delivery chamber 27, the application of pressure by the control unit against the delivery chamber's membrane may be used to force the air bubble to the IV solution source (through port 22), the air vent 24 (if it is capable of venting air in two directions) or the mixing chamber; to which of these three locations the bubble is directed depends on whether valve 31a, valve 31g or valve 31h is opened by the control unit.

After any bubble has been eliminated from the delivery chamber 27, the control unit takes a measurement of how much air is in the space defined by the control unit outside of and adjacent to the delivery chamber's membrane; in a preferred embodiment, the control unit uses an acoustic volume measurement system, such as that taught in U.S. Pat. No. 5,349,852 (which is also incorporated herein by reference). If the combined total volume of the delivery chamber and the space adjacent thereto is known, the amount of liquid in the delivery chamber may be determined by subtracting the measured volume of air from the known total volume.

Before any drugs are mixed, it may be desired to deliver some IV solution to the patient in order to establish flow through the line from the outlet 23 to the patient and through the patient's vein. In order to deliver liquid from the delivery chamber 27 to the patient, valve 32 is opened while the stopcock valve 33 is controlled and while pressure is applied to the delivery chamber's membrane by the control unit. (The valve 32 and stopcock valve 33 may be controlled in the manner described in U.S. Pat. No. 5,755,683, referenced hereinabove). The stopcock valve and pressure may be adjusted to control the rate of fluid delivered.

After an amount of fluid is delivered from the delivery chamber 27 to the patient, the volume of liquid delivered to the patient may be determined by taking another measurement of the volume of air defined by the control unit adjacent to and outside of the delivery chamber. Subtracting the volume of air measured before any liquid has been delivered from the volume of air measured after the liquid has been delivered provides the volume of liquid delivered to the patient. By using the acoustic volume measurement system of U.S. Pat. No. 5,349,852, and opening valve 32 and stopcock valve 33 at the same time the amount of liquid delivered may be tracked in real time as it is being delivered.

After the amount of liquid delivered from the delivery chamber 27 has been determined, the delivery chamber may be refilled by closing valve 32, as well as valves 31c–31i, and then opening valves 31a and 31b. The control unit again applies a negative pressure against the delivery chamber's membrane so as to draw liquid from the IV solution source into the delivery chamber 27. This additional IV solution may also be directed straight to the patient again in the manner described hereinabove, or it may be used in the admixture process in the mixing chamber. In a preferred embodiment, the volume of liquid in the delivery chamber is split, with a portion being delivered to the patient and the remainder being sent to the mixing chamber, where the liquid is used to reconstitute the drugs in the vials.

In order to reconstitute a powdered drug, liquid is introduced into the vial containing the powdered drug. With the cassette embodiment depicted in FIGS. 2–4, a mixing chamber 28 separate from the delivery chamber 27 is used to mix the IV solution with the drug. As noted above, it will be appreciated that, in an alternative embodiment, a single chamber may be used. In order to reconstitute the drug properly, it is important that the correct amount of IV solution be introduced into the vial. Typically, the correct volume of IV solution necessary to reconstitute the drug is more than the volume of the delivery chamber 27 (which in a preferred embodiment is 4 ml).

There are two basic types of drug preparation cycles: those drugs which come in powdered form requiring reconstitution, and those coming in liquid form which may or may not need dilution.

In a typical reconstitution cycle, IV solution is first introduced from the IV solution source into the delivery chamber 27. The control unit then determines whether there are any air bubbles in the delivery chamber 27 and, if there is none, makes a measurement of the volume of air defined by the control unit adjacent to and outside of the delivery chamber. With valves 31a–31g, 31i and 32 closed, and valves 31b and 31h opened, IV solution is forced from the delivery chamber 27 to the mixing chamber 28 by the control unit applying a positive pressure to the delivery chamber's membrane and/or a negative pressure to the mixing chamber's membrane. The volume of liquid delivered to the mixing chamber may be determined by taking another measurement of the volume of air defined by the control unit adjacent to and outside of the delivery chamber. Subtracting the volume of air measured before any liquid has been delivered to the mixing chamber 28 from the volume of air measured after the liquid has been delivered to the mixing chamber provides the volume of liquid delivered to the mixing chamber.

In order to introduce more IV solution into the mixing chamber, valve 31h is closed again and valve 31a opened to fill the delivery chamber 27 again with IV solution. Valve 31a is closed, a bubble-detection cycle is performed, and a measurement of the air volume is again taken. Then valve 31h is opened again, and IV solution is forced from the delivery chamber 27 to the mixing chamber 28. Another measurement of the air volume is taken in order to determine the volume of additional IV solution delivered to the mixing chamber. This cycle is repeated as often as necessary to introduce the correct amount of IV solution into the mixing chamber 28.

Once the mixing chamber 28 is filled with the desired amount of IV solution, the process of reconstituting the powdered drug may begin. In order to reconstitute the drug in vial 11a, valves 31d and 31i are opened, with all the other valves 31a–31c and 31e–31h kept closed. The control unit applies pressures to the membrane of the mixing chamber 28 to force the IV solution therein into the vial 11a.

Since the pressure within the vial often varies from the ambient (either being positively pressurized or having a partial vacuum), it is often desirable to check the pressure within the vial before the reconstitution process begins. It may be difficult to generate enough of a pressure differential between the mixing chamber 28 and the vial 11a to create a sufficiently strong spray to reconstitute the powdered drug, if the vial is positively pressurized. Since, it is usually preferable to bring the vial down to ambient pressure before the reconstitution process begins, it is preferred to check the vial pressure before the mixing chamber 28 is filled with IV solution. In order to check whether the vial 11a is positively pressurized, valves 31d and 31h are opened, with all the other valves 31a–31c, 31e–g and 31i kept closed; the mixing chamber 28 is kept substantially empty. If the vial 11a is positively pressurized, air escapes from the vial 11a into the mixing chamber 28. The control unit preferable includes a pressure transducer that measures the pressure of the mixing chamber 28 (as well as a pressure transducer that measures the pressure of the delivery chamber 27). The control unit measures whether there is an increase in the pressure of the mixing chamber 28; the presence and size of a pressure increase indicates whether and how much the vial 11a is pressurized. By applying a negative pressure against the mixing chamber's membrane additional air may be removed from the vial 11a to the mixing chamber 28, so as to bring the vial 11a to ambient. The mixing chamber 28 may be able to hold the excess air from the vial 11a along with the amount of IV solution necessary to reconstitute the drug in the vial 11a, or if there is too much excess air it may be forced from the mixing chamber 28 through valve 31i to the IV solution source (through port 22) or to the air vent 24 (if it is capable of venting air in two directions)—or even to another vial 11b or 11c if it has already been emptied.

If the vial 11a has a partial vacuum, the partial vacuum does not of course interfere with the delivery of IV solution from the mixing chamber 28 to the vial 11a. A partial vacuum may, however, interfere with the drawing of liquid from the vial back to the mix chamber. In order to eliminate a partial vacuum, air may be drawn from vent 24 into the vial 11a. One way to determine whether a partial vacuum exists in vial 11a is to fill the delivery chamber 27 with air (from the vent 24) and then, after valve 31g to the vent 24 is closed, opening valve 31d to permit fluid communication between the delivery chamber 27 and the vial 11a. The pressure in the delivery chamber 27 drops if the vial 11a has a partial vacuum. It is preferred that the vial be tested first for positive pressurization before being tested for a partial vacuum, so that if there is positive pressurization no powdered drug is accidentally blown into the delivery chamber 27, but rather is blown into the mixing chamber 28.

After the vial 11a is brought to ambient pressure (if necessary) and after the mixing chamber 28 is filled with the desired amount of IV solution, IV solution is sprayed into the vial 11a by the application of pressure by the control unit onto the mixing chamber's membrane. In order to ensure that the powdered drug is sufficiently mixed with the IV solution, the liquid is drawn back from the vial 11a into the mixing chamber 28, and then in a preferred embodiment, resprayed into the vial 11a. This process is repeated several times. Quickly sloshing the liquid back and forth between the vial 11a and the mixing chamber helps ensure that the powdered drug in vial 11a is fully dissolved by the IV solution.

Air pressure in the vial is managed during the repeated agitation to the mixing chamber by pulling and pushing air and fluid to and from the bottom and the top of the mixing chamber. Thus, flow into and out of the mixing chamber 28 is controlled by two valves, an upper valve 31h, which permits air to leave the mixing chamber before liquid leaves the mixing chamber, and a lower valve 31i, which permits liquid to leave the mixing chamber before air leaves the mixing chamber. The top port, shown in FIG. 2 as item 47, is used to introduce liquid into the mixing chamber and is used to remove air from the mixing chamber. The top port is shaped in accordance with the valve shown in FIGS. 22–24 of U.S. Pat. No. 5,755,683, so as to permit removal of any small air bubbles that may otherwise tend to collect at the port. (The top port 49 of the delivery chamber 27 has a similar design, since air bubbles need to be removed from the delivery chamber as well.) The mixing chamber's top port 47 is designed to remove air from the mixing chamber, since air of course tends to collect in the upper portion of the chamber. The bottom port 48 is used to remove liquid from the mixing chamber 28, since liquid of course tends to collect in the bottom portion of the mixing chamber.

Figure 5:
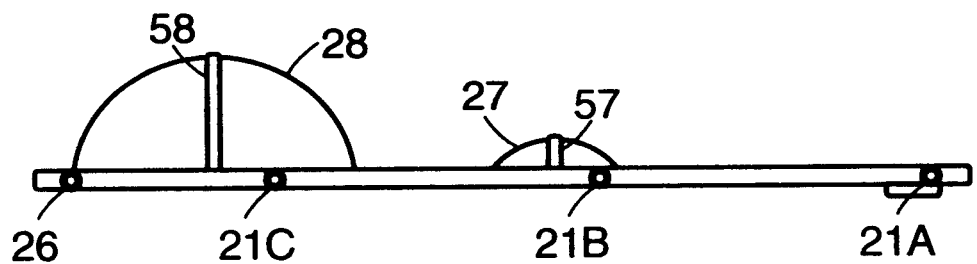
FIG. 5 is a top view of the back-plate component of the cassette of FIG. 3.
Figure 6:
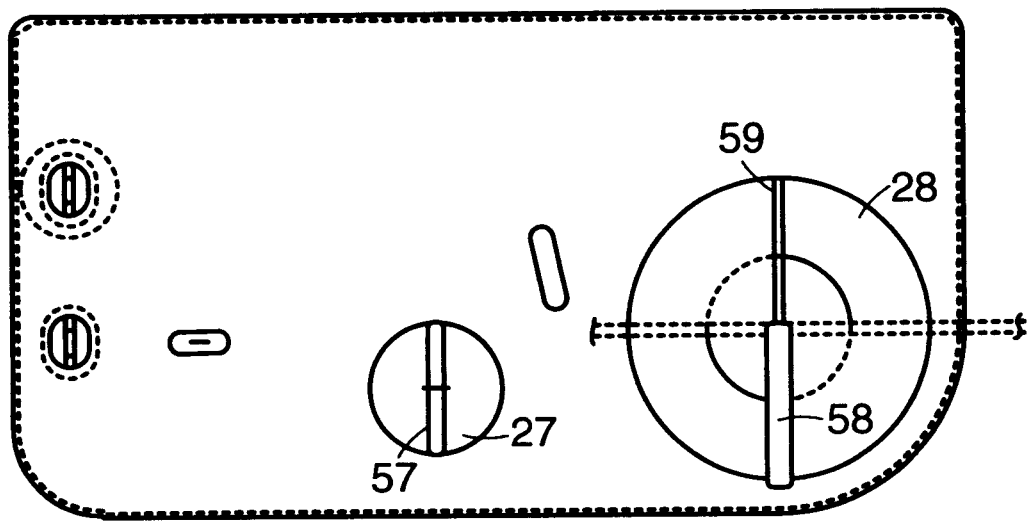
FIG. 6 is a front view of the back-plate component shown in FIG. 5.

As can be seen in FIGS. 5 and 6, which respectively show top and rear views of the back-plate component of the cassette, both the delivery chamber 27 and the mixing chamber 28 have channels formed into the rigid walls thereof. The channel 57 in the delivery chamber 27 permits easier flow into, out of and through the delivery chamber 27 when the membrane is resting against or near the rigid wall. As can be seen in FIG. 6, the upper portion 59 of the mixing chamber's channel is narrower than the channel's lower portion 58. The channel's lower portion 58 permits easier flow of liquid out of the mixing chamber 28 when the membrane is resting against or near the chamber's rigid wall. The difference in groove depth promotes the flow of air and liquid from the top and bottom of the chamber respectively while minimizing the total volume contained in the groove.

Once the powdered drug is completely reconstituted, it may be treated by the system as a liquid drug, which may or may not be diluted.

After the drug has been thoroughly mixed by sloshing the liquid back and forth between the mixing chamber 28 and the vial 11a, the drug is ready for delivery to the patient. If no further dilution of the drug is required, boluses of the drug are urged—by air pressure created by the control unit against the mixing chamber's membrane, or negative pressure applied against the delivery chamber's membrane—from the mixing chamber 28 to the delivery chamber 27. From the delivery chamber, these boluses of drug are delivered through valve 32 and stopcock valve 33 to the patient in the same manner described above for delivering straight IV solution to the patient.

If dilution of the drug is required, smaller boluses of the reconstituted drug may be urged from the mixing chamber 28 to the delivery chamber 27, into which additional IV solution may be introduced in the correct proportions from the IV solution source, in order to lower the concentration of the reconstituted drug. Once the drug in a bolus is diluted to the desired level, the drug may be delivered to the patient in the same manner described above. Each successive bolus is diluted and delivered in this manner. The control unit tracks the volume of drug delivered to the patient and the rate at which it was administered. Another method of diluting the drug is to introduce a volume of liquid from the IV fluid source into the mixing chamber to be mixed with the liquid drug.

If it is desired to supply to the patient only a fraction of the drug in the vial, the unused portion of the reconstituted drug may be returned to the vial 11a.

When, after providing several boluses of reconstituted drug to the delivery chamber 27, and the mixing chamber 28 is substantially emptied of the drug, any drug that may be in the manifold 45 or other passageway may be urged to the delivery chamber 27 by drawing air into the manifold from the vent 24, so that substantially all of the drug may be delivered to the patient before the next delivery cycle begins. In order to draw air in through the manifold 45, the air-vent valve 31g is opened and the delivery-chamber inlet valve 31b is opened, while all the other valves 31a, 31c–31f, 31h–31i, 32 are closed. The control unit applies a negative pressure to the membrane of the delivery chamber 27, so as to draw fluid through the manifold 45 into the delivery chamber. Air is thus drawn through the vent 24 to fill in after the drug being pulled through the manifold 45 into the delivery chamber 27. In the two-chambered system, air is also preferably drawn through the mixing chamber 28, in order to remove remants of the drug from the mixing chamber.

There are stages in the delivery cycle during which if air has been drawn into the delivery chamber 27, it is important to remove the air from the chamber 27 without removing any of the drug. (The acoustic volume measurement system, which is the preferred method used to measure the amount of liquid in the delivery chamber, does not work well if there is any bubble in the liquid.) To accomplish the removal of the air without permitting more than a tiny amount of reconstituted drug to escape, the delivery chamber is pressurized a little (with respect to the manifold) and valve 31b is opened and closed quickly; the chamber 27 is again checked for the presence of a bubble. These steps are repeated until no more air is detected. By keeping the pressure differential across the valve 31b relatively small and opening the valve for only a very short period of time, only a tiny amount, if any, of reconstituted drug can escape from the delivery chamber 27. If the valve is allowed to be only partially opened during this process, even less reconstituted drug can escape. Alternatively, the air may be pushed into the relatively small manifold volume to control how much is released.

Before beginning a new delivery cycle, it may be desirable to clean any small amounts of the first drug from the passageways 25 so that the two drugs do not mix. This cleansing of the cassette's passageways may be accomplished by drawing IV solution from the IV solution source and passing the IV solution into and out of the delivery chamber 27 (where the amount of IV solution may be measured), through the manifold 45 and through the mixing chamber 28. The emptied vial may also be rinsed. A sufficient amount of IV solution should be introduced into the cassette 17 at this point in order to dilute to a safe, negligible concentration whatever remnants of the drug remain in the cassette so that the IV solution used to cleanse the cassette may be sent to the patient. The amount of IV solution used should be enough to ensure that the cassette is properly rinsed so that residue of the prior drug does not interact with the next drug.

It may be desired to deliver to the patient additional straight IV solution before delivering the next drug from vial 11b. When it is time to prepare and deliver the drug from vial 11b, the drug is prepared and delivered in the same manner as described above in connection with preparing and delivering the drug from vial 11a. After the drug from vial 11b has been prepared and delivered to the patient, and after the cassette is cleansed of any remnants of the drug from vial 11b, the drug from vial 11c may in turn be prepared and delivered to the patient.

Depending on the desired treatment, the liquid drug provided to the cassette through port 26 may be provided to the patient before, between or after the delivery of the drugs in the vials 11a–11c. The liquid drug provided through port 26 of course does not have to reconstituted; it may however need to be diluted prior to delivery.

The above-described system may be used in a variety of ways. For instance, the vials may be accessed in different orders (for example, vial 11b, then 11c and then 11a, or first vial 11c, then 11a and then 11b). A vial may contain a powdered drug, which may be reconstituted, then diluted and then delivered, or which may simply be reconstituted and delivered. A vial may also contain a liquid drug, which may likewise be diluted and delivered, or simply be delivered straight. A drug may also be provided through the luer port 26 to be diluted and delivered, or simply delivered. The luer port 26 may also provide a second IV fluid for use in reconstitution and/or dilution. Providing a secondary IV fluid through luer port 26, as well as a primary IV fluid through port 22, is an important feature if the vials attached to the cassette contain drugs that require different types of fluids to be reconstituted and/or diluted properly.

When the cassette 17 is removed from the control unit 15, the control unit is no longer able to control the membrane-based valves 31a–31i, 32 and the stopcock valve 33. Each membrane-based valve assumes an open position if not being actuated by the control unit, and the stopcock valve 33 remains in an open position, if it had been in an open position when the cassette was removed from the control unit. Without the outlet free-flow-prevention valve 35 shown in FIGS. 2 and 3, concentrated drug could be accidentally delivered at an excessively high flow rate to the patient. Without the inlet free-flow-prevention valve 34 shown in FIGS. 2 and 3, concentrated drug may make its way out of the inlet port 22 to the IV solution source 13, thereby contaminating the IV solution source so that it cannot be safely used again. In addition, multiple drugs in the cassette and/or vial can mix creating hazardous and uncontrolled solutions.

The inlet and outlet free-flow-prevention valves 34 and 35 are acted on by actuators mounted in the control unit's door when the cassette 17 is removed from the control unit 15. When the door is opened, these actuators push the membranes of the free-flow-prevention valves 34 and 35 into a closed position, and the membranes are shaped to remain in a closed position permanently once they are actuated. Thus, the removal of the cassette from the control unit closes the two free-flow-prevention valves 34 and 35 and prevents liquid from flowing from the cassette to either the patient or the IV solution source.

FIGS. 7–10 show several views of a membrane used in a preferred embodiment of the free-flow-prevention valves 34 and 35 shown in FIGS. 2 and 3. The membrane includes a central plug portion 72, a rib 76 for mounting the membrane in the rigid cassette body, and a relatively thin, folded portion 74 that connects the plug portion 72 and the rib 76. When the actuator pushes the exterior end 82 of the plug portion 72, the interior end 83 of the plug portion is urged into the fluid passageway (which leads to either the cassette's IV solution inlet 22 or the cassette's liquid outlet 23). The folded portion 74 is folded further by this action, such that the plug portion 72 is held in the closed position blocking the fluid passageway.

Thus, removal of the cassette 17 from the control unit 15 causes the free-flow-prevention valves 34, 35 to be closed in such a way that they cannot be easily opened, so that they are essentially permanently closed. Thus, the cassette can no longer be used. If the cassette is re-inserted into the control unit, the control unit senses an occlusion upstream when it attempts to draw IV solution from the IV solution source, or it senses an occlusion downstream when it tries to deliver liquid to the patient. The control unit, in a preferred embodiment, sounds an alarm after several attempts are made to pump liquid into or out of the cassette. In an alternative embodiment, the cassette may be provided, in addition to the free-flow-prevention valves, with a break-away tab that is broken off by an actuator when the cassette is removed from the control unit. When a cassette of this type is inserted into the control unit, the control unit determines whether the break-away tab is present on the cassette. If such a tab is present, the control unit proceeds as normal, checking for occlusions, etc. If the tab is missing, the control unit sounds an alarm indicating that the cassette has been used already, and a new cassette should be inserted. The break-away tab thus allows the control unit to avoid performing several occlusion checks if the cassette has already been used.

The control unit may also be programmed to sound alarms when other potentially dangerous situations occur, and the control unit preferably includes a keypad so that information regarding the desired drug delivery cycles for a given patient may be entered into the system so that the drugs may be prepared and delivered according the desired cycles. Information regarding the patient may also be entered into or read by the control unit, as well as information regarding the medical provider who is entering the information. Information regarding the proper, safe dosage levels for various drugs may be programmed into the control unit, so that if, for example, the medical provider attempts to enter a dosage level that is greater than what is normally permitted, the control unit sounds an alarm. The control unit may also be programmed to prevent the delivery of an unsafe dosage, or it may be programmed so that a medical provider with sufficient authority may override the programmed maximum dosage levels.

In a preferred embodiment, the control unit is connected to a hospital-wide network, so that information in the control unit may be updated easily. For instance, information regarding the patient, such as weight and drug allergies, may be entered into the hospital network at admissions. When the patient is to be connected to the drug-preparation-and-delivery system described hereinabove, the patient's identification code may be entered into or read by the control unit, and the control unit can then access the network so that the patient's information is available to permit the control unit to sound an alarm if the patient's drug allergies or low weight could create a dangerous situation based on the drugs that are to be delivered or drug delivery cycles that are to be implemented. A list of dangerous drug interactions may be kept and updated by the pharmacy as well. All drugs provided to the patient, including the drugs administered by the drug-preparation-and-delivery system described hereinabove, as well as drugs provided by traditional means, may be recorded in the hospital network, and the control unit may sound an alarm is a dangerous interaction may occur. Likewise, proper dosage and delivery-cycle information may be kept and updated by the hospital's pharmacy, so as to provide the framework for safe drug delivery. If the desired drug delivery cycle entered into the control unit does not fall within the safety framework, the control unit may sound an alarm.

The control unit may also store information regarding the drugs delivered to the patient and the time frames of the deliveries. This information may be downloaded into the network, so that it is available for later review by a medical provider, and so that the patient (or the patient's insurance company) may be properly billed for the drugs that are actually delivered to the patient.

Although the invention has been described with reference to several preferred embodiments, it will be understood by one of ordinary skill in the art that various modifications can be made without departing from the spirit and the scope of the invention, as set forth in the claims hereinbelow.

What is claimed is:

1. A method for mixing a drug provided in a vial, the method comprising:

provided a fluid passageway in fluid communication with a vial receptacle and with a top and a bottom of a variable-volume chamber;

providing an air vent in fluid communication with the fluid passageway;

moving liquid from the bottom of the chamber, through the fluid passageway and the vial receptacle, to the vial;

moving air from the top of the chamber, through the fluid passageway and the vial receptacle, to the vial; and moving liquid from the vial, through the vial receptacle and the fluid passageway, to the chamber.

2. A method according to claim 1, further including moving air from the vial, through the vial receptacle and the fluid passageway, to the chamber.

3. A system for mixing a drug provided in a vial, the vial having an interior, the system comprising:

a fluid passageway;

a vial receptacle for providing fluid communication between the fluid passageway and the interior of the vial;

a variable-volume chamber having a top and a bottom;

a top port providing fluid communication between the fluid passageway and the top of the chamber;

a bottom port providing fluid communication between the fluid passageway and the bottom of the chamber;

an air vent in fluid communication with the fluid passageway; and a valving mechanism adapted to control flow through the top port, the bottom port, and the air vent.

4. A system according to claim 3, wherein the valving mechanism is adapted to permit, at separate times, air to flow from the top port to the vial and liquid to flow from the bottom port to the vial.

* * * * *

UNITED STATES PATENT AND TRADEMARK OFFICE
CERTIFICATE OF CORRECTION

PATENT NO. : 6,234,997 B1
DATED : May 22, 2001
INVENTOR(S) : Dean L. Kamen, et al.

It is certified that error appears in the above-identified patent and that said Letters Patent is hereby corrected as shown below:

<u>Title page, item [54],</u>
Title of the Invention, replace "for Mixing and Delivering Intravenous Drugs" with -- for Mixing Intravenous Drugs --.

<u>Column 1,</u>
Lines 1 and 2, replace "for Mixing and Delivering Intravenous Drugs" with -- for Mixing Intravenous Drugs --.

Signed and Sealed this

Thirteenth Day of November, 2001

*Attest:*

NICHOLAS P. GODICI
*Attesting Officer*     *Acting Director of the United States Patent and Trademark Office*